(12) United States Patent
Zimmerling et al.

(10) Patent No.: US 8,620,444 B2
(45) Date of Patent: Dec. 31, 2013

(54) IMPLANT SENSOR AND CONTROL

(75) Inventors: Martin Zimmerling, Patsch (AT); Ingeborg Hochmair, Axams (AT); Erwin Hochmair, Axams (AT); Martin Kerber, Innsbruck (AT); Werner Lindenthaler, Oberperfuss (AT); Peter Nopp, Birgitz (AT); Marcus Schmidt, Innsbruck (AT); Hansjörg Schoesser, Reith im Alpbachtal (AT); Clemens Zierhofer, Kundl (AT)

(73) Assignee: Med-El Elektromedizinische Geraete GmbH, Innsbruck (AT)

(*) Notice: Subject to any disclaimer, the term of this patent is extended or adjusted under 35 U.S.C. 154(b) by 1414 days.

(21) Appl. No.: 12/034,264

(22) Filed: Feb. 20, 2008

(65) Prior Publication Data

US 2008/0200779 A1 Aug. 21, 2008

Related U.S. Application Data

(60) Provisional application No. 60/890,685, filed on Feb. 20, 2007.

(51) Int. Cl.
*A61N 1/08* (2006.01)

(52) U.S. Cl.
USPC .............................. 607/57; 607/63

(58) Field of Classification Search
USPC ...................................... 607/55–57
See application file for complete search history.

(56) References Cited

U.S. PATENT DOCUMENTS

| 4,127,134 | A | 11/1978 | Ushakoff | 128/419 |
| 4,332,256 | A | 6/1982 | Brownlee et al. | 128/419 PT |
| 4,619,653 | A | 10/1986 | Fischell | 604/891 |
| 5,571,148 | A * | 11/1996 | Loeb et al. | 607/57 |
| 7,571,006 | B2 * | 8/2009 | Gordon et al. | 607/57 |
| 2006/0129202 | A1 | 6/2006 | Armstrong | 607/45 |

FOREIGN PATENT DOCUMENTS

WO WO 2008/103717 8/2008 ............ A61N 1/36

* cited by examiner

*Primary Examiner* — Luther Behringer
(74) *Attorney, Agent, or Firm* — Sunstein Kann Murphy & Timbers LLP

(57) ABSTRACT

An implant includes a humidity sensor for generating a signal indicative of humidity within the implant. A controller within the implant receives the signal indicative of humidity, and controls the implant based on the signal indicative of humidity.

6 Claims, 2 Drawing Sheets

IMPLANT SENSOR AND CONTROL

CROSS REFERENCE TO RELATED APPLICATIONS

This application claims the benefit of U.S. Provisional Application No. 60/890,685, filed Feb. 20, 2007, which is hereby incorporated herein by reference in its entirety.

TECHNICAL FIELD AND BACKGROUND ART

The present invention relates to implants, and more particularly, to sensing and responding to humidity or another condition within an implant.

BACKGROUND ART

Often an implant is hermetically sealed to prevent build-up of moisture within the implant. The moisture buildup within the implant may adversely affect the electronic circuits within the implant. For example, moisture buildup in the implant may cause incorrect stimulation, such as over-stimulation or stimulation including direct current and/or exceeding charge density per phase limits.

Determination of moisture build-up within an implant can be problematic. Subjective feedback from the patient regarding implant stimulation behavior is often difficult, particularly with younger patients. Another approach is to incorporate a humidity sensor/switch within the implant. An exemplary telemetry system for remotely monitoring sensed humidity within a pacemaker is disclosed in U.S. Pat. No. 4,332,256 (Brownlee et al.), which is incorporated herein by reference in its entirety. However, interpretation of telemetry data received from the implant is often difficult with corrective measures performed in an untimely and/or inconvenient manner.

SUMMARY OF THE INVENTION

In accordance with one embodiment of the invention there is provided an implant that includes a humidity sensor for generating a signal indicative of humidity within the implant. A controller within the implant receives the signal indicative of humidity, and controls the implant based on the signal indicative of humidity.

In accordance with related embodiments of the invention, the implant may be a cochlear implant, wherein the implant includes a stimulator for stimulating an array of electrodes. The controller may inhibit output of the stimulator based on the signal indicative of humidity. The controller may control the stimulator to stimulate the electrodes so as to produce a perceived alert based on the signal indicative of humidity. The alert may be produced for a predetermined duration upon turning on of the implant.

In accordance with further related embodiments of the invention, the controller may turn power off based on the signal indicative of humidity. The implant may include a battery, wherein the controller discharges the battery based on the signal indicative of humidity. The implant may further includes a hydrophilic agent positioned with the implant so as to direct moisture to a desired location within the implant. The humidity sensor may be positioned substantially adjacent the hydrophilic agent.

In accordance with another embodiment of the invention, a method of controlling a cochlear implant is presented. The implant includes a stimulator for stimulating an array of electrodes. The method includes generating a signal indicative of humidity within the implant. The implant is controlled based on the signal indicative of humidity, wherein the generating and controlling is performed within the implant.

In accordance with related embodiments of the invention, controlling the implant may include inhibiting output of the stimulator based on the signal indicative of humidity. Controlling the implant may include controlling the stimulator to stimulate the electrodes so as to produce a perceived alert based on the signal indicative of humidity. The alert may be produced for a predetermined duration upon turning on of the implant. Controlling the implant may include turning power off based on the signal indicative of humidity. The implant may include a battery, wherein controlling the implant includes discharging the battery based on the signal indicative of humidity.

In accordance with another embodiment of the invention, an implant includes a humidity sensor for generating a signal indicative of humidity within the implant. A controller means within the implant receives the signal indicative of humidity and controls the implant based on the signal indicative of humidity.

In accordance with related embodiments of the invention, the implant may be a cochlear implant, wherein the implant includes a stimulator for stimulating an array of electrodes. The controller means may inhibit output of the stimulator based on the signal indicative of humidity. The controller means may control the stimulator to stimulate the electrodes so as to produce a perceived alert based on the signal indicative of humidity. The alert may be produced for a predetermined duration upon turning on of the implant. The controller means may turn power off based on the signal indicative of humidity. The implant may include a battery, wherein the controller means may discharge the battery based on the signal indicative of humidity. A hydrophilic agent may be positioned with the implant so as to direct moisture to a desired location within the implant. The humidity sensor may be positioned substantially adjacent the hydrophilic agent.

In accordance with another embodiment of the invention, a computer program product for placing within, and controlling, a cochlear implant is presented. The implant includes a stimulator for stimulating an array of electrodes, and a humidity sensor for generating a signal indicative of humidity within the implant. The computer program product includes a computer usable medium having computer readable program code thereon. The computer readable program code includes program code for controlling the implant based on the signal indicative of humidity.

In accordance with related embodiments of the invention, the program code for controlling the implant may include program code for inhibiting output of the stimulator based on the signal indicative of humidity. The program code for controlling the implant may include program code for controlling the stimulator to stimulate the electrodes so as to produce a perceived alert based on the signal indicative of humidity. The alert may be produced for a predetermined duration upon turning on of the implant.

In accordance with another embodiment of the invention, a method of controlling an implant includes performing a self-test at the implant. A signal indicative of a result of the performed self-test is generated. The implant is controlled based on the signal, wherein the performing, generating and controlling is performed within the implant.

In accordance with related embodiments of the invention, the signal may be indicative of humidity. The implant may be a cochlear implant, the cochlear implant including a stimulator for stimulating an array of electrodes, and wherein controlling includes inhibiting output of the stimulator based on the signal. Controlling the implant may include controlling the stimulator to stimulate the electrodes so as to produce a perceived alert based on the signal indicative of humidity. The alert may be produced for a predetermined duration upon turning on of the implant. An externally audible alert based on the signal may be provided.

In accordance with further related embodiments of the invention, controlling the implant may include turning power off based on the signal. The implant may include a battery, and controlling the implant may include discharging the battery based on the signal. The self-test may be initiated by the implant. The self-test may be initiated periodically or upon implant power-on.

In accordance with another embodiment of the invention, a computer program product for placing within, and controlling, an implant, is presented. The computer program product includes computer usable medium having computer readable program code thereon. The computer readable program code includes program code for performing self-test at the implant, the self-test generating a signal indicative of a result of the performed self-test. The computer program product further includes program code for controlling the implant based on the signal.

In accordance with related embodiments of the invention, the implant may include a humidity sensor, and the signal is indicative of humidity within the implant. The implant may include a stimulator for stimulating an array of electrodes, wherein the program code for controlling the implant includes program code for inhibiting output of the stimulator based on the signal. The program code for controlling the implant may include program code for controlling the stimulator to stimulate the electrodes so as to produce a perceived alert based on the signal. The alert may be produced for a predetermined duration upon turning on of the implant. The program code for controlling the implant may generate an externally audible alert. The program code for performing self-test may initiate the self-test, for example, periodically or upon implant power-on.

In accordance with another embodiment of the invention, an implant includes a self-test module for generating a signal indicative of a condition within the implant. A controller within the implant receives and controls the implant based on the signal.

In accordance with related embodiments of the invention, the signal may be indicative of humidity. The implant may be a cochlear implant, wherein the implant includes a stimulator for stimulating an array of electrodes. The controller may inhibit output of the stimulator based on the signal. The controller may control the stimulator to stimulate the electrodes so as to produce a perceived alert based on the signal. The alert may be produced for a predetermined duration upon turning on of the implant. The controller may provide an externally audible alert. The controller may turn power off based on the signal. The implant may include a battery, wherein the controller discharges the battery based on the signal.

In accordance with still another embodiment of the invention, an implant includes a sensor for generating a signal indicative of an environmental condition within the implant. A controller within the implant receives the signal indicative of the environmental condition, and controls the implant based on the signal indicative of the environmental condition.

In related embodiments of the invention, the controller may control the implant based on a deviation of the sensed environmental condition from a desired environmental condition. The environmental condition may be a temperature, a humidity, and/or a concentration of one or more gases.

In accordance with yet another embodiment of the invention, a method of controlling a cochlear implant is presented. The implant includes a stimulator for stimulating an array of electrodes. The method includes generating a signal indicative of an environmental condition within the implant. The implant is controlled based on the signal indicative of the environmental condition, wherein the generating and controlling is performed within the implant.

In related embodiments of the invention, controlling the implant may be based on a deviation of the sensed environmental condition from a desired environmental condition The environmental condition may be a temperature, a humidity, and/or a concentration of one or more gases.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments, a sensor and/or self-test module is exploited by a controller within the implant for various control and switching functions. Thus, there is no need to rely on patient feedback, or interpretation of telemetry data, to monitor and react to changes in implant humidity. The sensor may be, for example, a humidity sensor, a temperature sensor, and/or a concentration of one or more gases. Details are discussed below.

Figure 1:
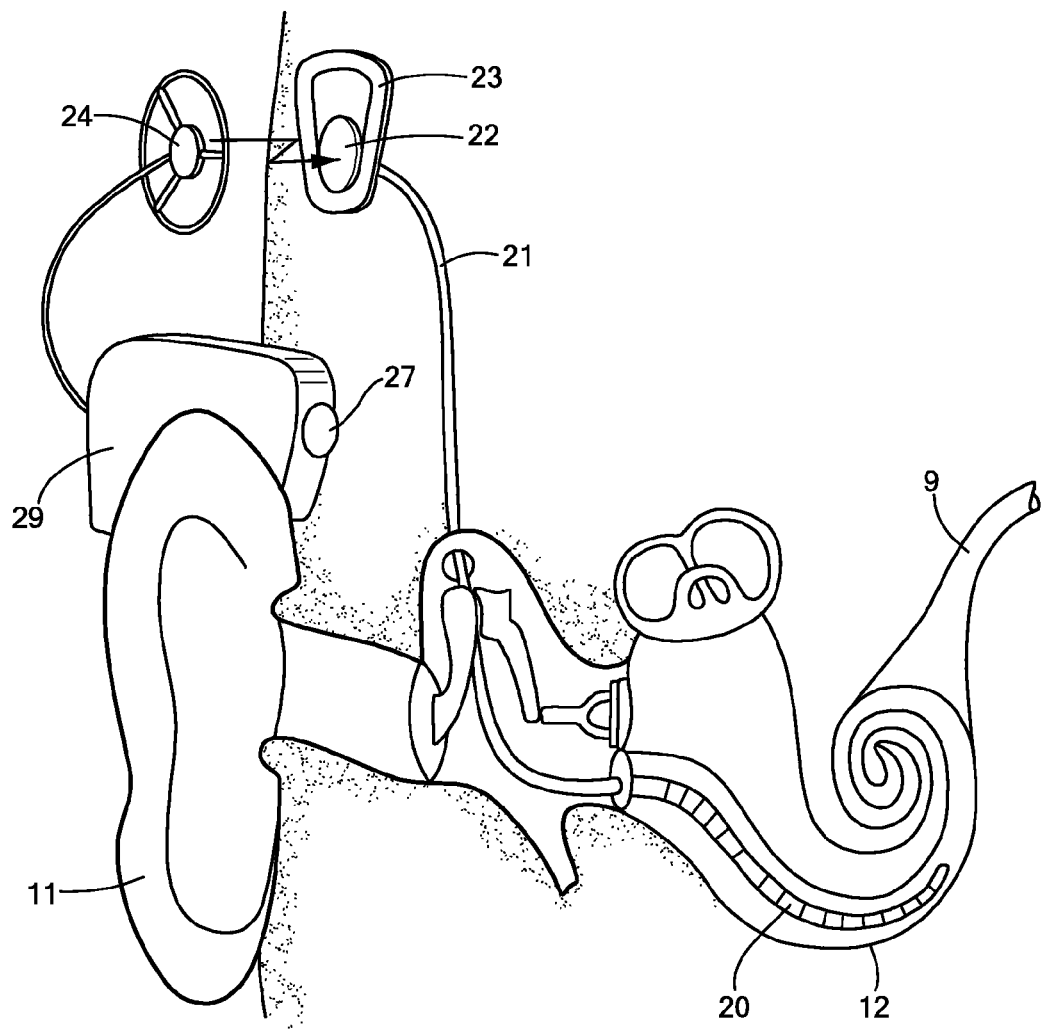
FIG. 1 shows a conventional cochlear prosthesis.

FIG. 1 shows an exemplary cochlear implant. It is to be understood that the present invention is not limited to a cochlear prosthesis, and that the present invention is applicable to other types of implants, as known in the art.

The cochlear implant typically includes two parts, an external component including a microphone 27 and a speech processor 29, and an implanted component that includes a stimulator 23. The speech processor 29 includes the power supply (batteries) of the overall system and is used to perform signal processing of the acoustic signal received by the microphone 27 to extract the stimulation parameters. Attached to the speech processor 29 is a transmitter coil 24 that transmits power and data signals to the implanted unit transcutaneously via a radio frequency (RF) link. The implanted component includes a receiver coil 22 that is capable of receiving the data and/or power from the transmitter coil 24. Based on the received data, the stimulator 23 sends stimulation signals via a cable 21 to an electrode array 20 positioned in the cochlea 12, stimulating the auditory nerve 9. It is to be understood that in various embodiments of the invention, various parts or all of the cochlear may be implanted. An exemplary fully implantable is described in U.S. Pat. No. 6,272,382 (Faltys et al.), incorporated herein by reference in its entirety. Furthermore, in various embodiments both the external component and the internal component may include a processor, with various functionality split between the two processors.

Figure 2:
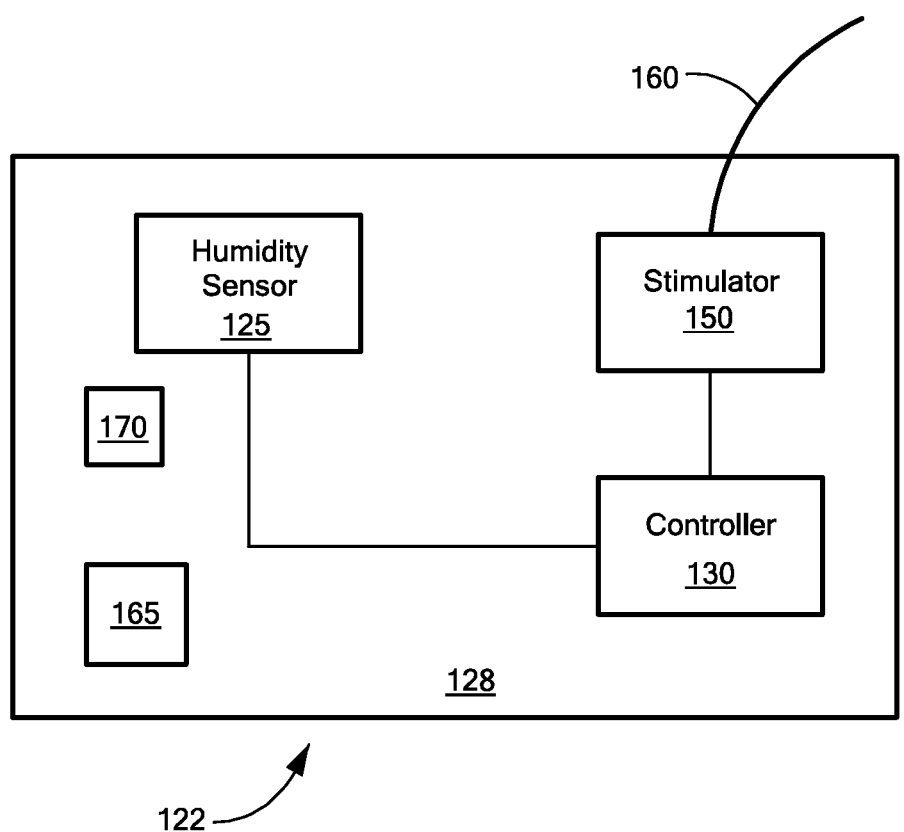
FIG. 2 is a block diagram showing a cochlear implant system that implements sensing and control, in accordance with one embodiment of the invention.

FIG. 2 is a block diagram showing various elements of an implanted component 122 of a cochlear implant system, in accordance with one embodiment of the invention. The implanted component typically includes a hermetically sealed housing 128, which may be made of, without limitation, titanium, nonmagnetic stainless steel, or a ceramic.

The implanted component 122 includes a sensor 125, such as a humidity sensor 125 which generates a signal indicative of humidity within the implant. The humidity sensor 125 may be, without limitation, a capacitive or resistive humidity sensor, as known in the art. It is to be understood that instead of, or in addition to, a humidity sensor, other types of sensors known in the art, such as a temperature sensor, motion sensor, and/or gas sensor, may be used in accordance with the invention described herein, that provide a signal indicative of one or more conditions, such as an environmental condition, within the implant. In various embodiments, the implant may include a self-test module. The self-test module may initiate various tests within the implant, and/or receive input from one or more sensors, and provide a signal indicative of the performed self-test or a sensed condition. The self-test module may initiate, without limitation, self-test periodically or upon implant power-on.

A controller 130 is positioned within the implanted component 122. The controller 130 is operationally coupled to, and receives the signal from the sensor 125 and/or self-test module. In various embodiments, the controller 130 may be, for example, electrically coupled to the sensor 125 and/or self-test module.

In illustrative embodiments of the invention, the controller 130 controls the implant based on the signal received from the sensor 125 and/or self-test module. Since both the controller 130 and the sensor 125 is positioned within the implanted component 122, control of the implant based on sensed signal and/or self-test is advantageously performed without having to externally send or process telemetry data, and without patient interaction.

The controller 130 may include, without limitation, a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), memory, or any other means including any combination thereof. Memory may include, for example, a diskette, a fixed disk, a Compact Disk (CD), Read Only Memory (ROM), Erasable Programmable Read-Only Memory (EPROM), and/or Random Access Memory (RAM). Computer program logic implementing all or part of the functionality previously described herein may be embodied in various forms, including, but in no way limited to, a source code form, a computer executable form, and various intermediate forms (e.g., forms generated by an assembler, compiler, linker, or locator.) Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The controller 130 may command various functionality based on the signal received from the sensor 125 and/or self-test module. Deviations from a desired environmental condition may trigger the command and control. For example, in receiving signals from a humidity sensor, at the beginning ingress of humidity the controller 130 may cause stimulator 150 to stimulate electrode array 160 to produce a perceived alert to the person wearing the cochlear implant. Note that such an alert is perceived only by the person wearing the cochlear implant, who can then proceed, for example, to see an audiologist for a telemetry check (which may include reading out relative humidity). In other embodiments, the controller 130 may cause an externally audible alert when, for example, the speech processor is attached. Instead of an audible alert, other types of alerts may be provided, such as a visual alert.

The alert provided may last for a predetermined duration upon turning on the implant. For example, when turning on the implant, three short beeps may be provided. Of course, other alerts may be provided upon further ingress, or at various levels, of humidity or other condition within the implant.

Upon further ingress of humidity (or other condition within the implant), or at, for example, a predetermined humidity level, the controller 130 may inhibit stimulation at the electrode array 160, thus avoiding any current flow at the electrodes. In various embodiments, the controller 130 may switch power off in the implant and/or discharge an implanted battery 165 in a controlled fashion. In still further embodiments, the resonance frequency and/or the quality factor of the RF circuit on the implant side may be changed.

In various embodiments, a hydrophilic agent 170, such as silica gel, may be positioned in the internal component 122 to concentrate moisture at a desired location. For example, the hydrophilic agent 170 may be positioned in close proximity to the humidity sensor 125. Water vapor is thus concentrated at the hydrophilic agent 170, and consequently at the humidity sensor 125, increasing the implant's sensitivity to humidity.

In various embodiments, the disclosed method may be implemented as a computer program product for use with a computer system. Such implementation may include a series of computer instructions fixed either on a tangible medium, such as a computer readable media (e.g., a diskette, CD-ROM, ROM, or fixed disk) or transmittable to a computer system, via a modem or other interface device, such as a communications adapter connected to a network over a medium. Medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable media with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of controlling a cochlear implant, the implant including a stimulator for stimulating an array of electrodes, the method comprising:
 positioning a hydrophilic agent in the implant so as to direct moisture to a desired location within the implant;
 positioning a humidity sensor substantially adjacent the hydrophilic agent;
 generating, by the humidity sensor, a signal indicative of humidity within the implant; and
 controlling the implant based on the signal indicative of humidity, wherein the generating and controlling is performed within the implant, and wherein controlling includes controlling the stimulator to stimulate the electrodes so as to produce a perceived audio alert based on the signal indicative of humidity.

2. The method of claim 1, wherein controlling the implant includes inhibiting output of the stimulator based on the signal indicative of humidity upon further ingress of humidity.

3. The method according to claim 1, wherein the alert is produced for a predetermined duration upon turning on of the implant.

4. The method according to claim 1, wherein controlling the implant includes providing an externally audible alert based on the signal indicative of humidity.

5. The method according to claim 1, wherein controlling the implant includes turning power off based on the signal indicative of humidity upon further ingress of humidity.

6. The method according to claim 1, wherein the implant includes a battery, and wherein controlling the implant includes discharging the battery based on the signal indicative of humidity.

* * * * *